United States Patent [19]

Wilms et al.

[11] 4,081,404
[45] Mar. 28, 1978

[54] OLIGOMERIZATION OF UNSATURATED HYDROCARBONS WITH A MOLYBDENUM CATALYST

[75] Inventors: Elmar Wilms, Dusseldorf-Benrath; Georg Michalczyk, Neukirchen-Vluyn, both of Germany

[73] Assignee: Deutsche Texaco Aktiengesellschaft, Hamburg, Germany

[21] Appl. No.: 751,934

[22] Filed: Dec. 17, 1976

Related U.S. Application Data

[62] Division of Ser. No. 625,966, Oct. 28, 1975.

[30] Foreign Application Priority Data

Oct. 28, 1974 Germany .............................. 2451127

[51] Int. Cl.² .......................... B01J 27/02; C07C 3/10
[52] U.S. Cl. ............................. 252/439; 260/683.15 R
[58] Field of Search ................ 252/439; 260/683.15 R

[56] References Cited

U.S. PATENT DOCUMENTS

| | | | |
|---|---|---|---|
| 2,399,927 | 5/1946 | Howes et al. | 252/439 |
| 2,426,483 | 8/1947 | Boucher et al. | 252/439 X |
| 2,435,380 | 2/1948 | Archibald et al. | 252/439 |
| 2,446,619 | 8/1948 | Stewart et al. | 252/435 X |
| 3,058,896 | 10/1962 | Nahin | 252/439 |
| 3,416,893 | 12/1968 | Parish et al. | 252/439 X |
| 3,519,573 | 7/1970 | Coe | 252/439 |
| 3,658,927 | 4/1972 | Crain et al. | 252/439 X |
| 3,686,137 | 8/1972 | Gatti | 252/439 X |
| 3,830,752 | 8/1974 | Mickelson | 252/439 X |

Primary Examiner—Patrick P. Garvin
Assistant Examiner—William G. Wright
Attorney, Agent, or Firm—Thomas H. Whaley; Carl G. Ries; George J. Darsa

[57] ABSTRACT

A process for oligomerizing unsaturated hydrocarbons having 2 to 5 carbon atoms in the molecule employing a novel molybdenum-containing carrier catalyst.

5 Claims, No Drawings

OLIGOMERIZATION OF UNSATURATED HYDROCARBONS WITH A MOLYBDENUM CATALYST

This is a division of application Ser. No. 625,966, filed Oct. 28, 1975.

BACKGROUND OF THE INVENTION

The present invention relates to a method for producing novel molybdenum-containing supported catalysts and to a process for oligomerizing unsaturated hydrocarbons having 2 to 5 carbon atoms in the molecule in the presence of the novel catalysts.

It is known from Asigner, "Die Petrolchemische Industrie" volume I, pp. 275 (1971) to oligomerize lower olefins with acids or acid-containing catalysts. In this connection, phosphoric acid or phosphoric acid-containing catalysts have proven to be preferable. However, acidic catalysts have the disadvantage of being sensitive to sulfur, ammonia, amines and acetylene, thereby requiring that such substances be substantially removed from the gaseous olefins prior to oligomerization. In addition, when the reaction conditions during oligomerization of olefins with acids are not closely adhered to, considerable amounts of non-olefinic by-products are obtained as a result of hydropolymerization.

Furthermore, it is known to perform selective di-, tri- and polymerization of certain lower olefins employing such catalysts as, for example, Ziegler-Natta catalysts and catalysts comprising cobalt on activated carbon as well as with alkali metals and aluminum chloride. Moreover, a number of other metals were tested with regard to their activity as oligomerization catalysts including, for example, a supported $MoO_3$ catalyst. Such catalysts, however, preferably disproportionate olefins. Thus, for example, from 2 molecules of propylene essentially butene and ethylene are obtained and only a small amount of propylene is oligomerized to $C_6$-hydrocarbons.

U.S. Pat. No. 2,446,619 suggests to use the oxide of molybdenum and phosphoric acid on a suitable support, such as silica gel, as catalyst for oligomerization where the dimerization of lower olefins is preferred. The reference reports that in the absence of hydrogen and utilizing a temperature of about 550° to 600° F. and a pressure of 200 p.s.i.g. only 12 weight percent of liquid product basis the olefin feed was provided. The addition of hydrogen to the gaseous olefins raised the liquid product to 25.7 weight percent. Similar results are reported with another modified molybdenum-containing carrier catalyst.

According to U.S. Pat. No. 2,446,619, a plurality of materials are suggested as catalysts. One type includes variable valent metals active for the hydrogenation and dehydrogenation, e.g. tungsten, vanadium, molybdenum and chromium, used in the oligomerization catalyst in the form of an oxide or sulfide. Since no further mention or examples are provided regarding the sulfides, this suggests that catalysts containing, for example, molybdenum sulfide are less effective than catalysts containing molybdenum oxide. Our experiments with catalysts containing molybdenum sulfide showed that such catalysts are practically inactive for both the oligomerization and the disproportionation of unsaturated hydrocarbons having 2 to 5 carbon atoms in the molecule.

It is an object of this invention to provide a process for oligomerizing unsaturated hydrocarbons in high yields.

Another object of this invention is to provide a new catalyst for oligomerizing unsaturated hydrocarbons having 2 to 5 carbon atoms in the molecule.

Another object of this invention is to provide an oligomerization process wherein $C_2$ to $C_5$ unsaturated hydrocarbons are selectively converted to higher olefinically unsaturated hydrocarbons where said process produces essentially no saturated by-products by hydropolymerization.

Yet another object is to provide a catalyst that is substantially insensitive to sulfur, ammonia, amine or acetylene components in the olefin feedstock.

Other objects and advantages will become apparent from a reading of the following detailed description and examples.

DESCRIPTION OF THE INVENTION

Broadly, this invention contemplates a process for oligomerizing an unsaturated hydrocarbon having 2 to 5 carbon atoms which comprises contacting said hydrocarbon in the presence of a sulfur containing molybdenum supported catalyst, said catalyst prepared by heating a composite comprising a sulfur containing molybdenum compound on a support at a temperature of about 300° to 700° C. in an oxidizing atmosphere.

In another embodiment, this invention contemplates a method for preparing a sulfur containing molybdenum supported catalyst which comprises heating a composite comprising a sulfur containing molybdenum compound on a support at a temperature of about 300° to 700° C. in an oxidizing atmosphere.

The novel catalysts provided by this invention and employed in the oligomerization process described herein are prepared from composites comprising a sulfur containing molybdenum compound and a catalyst carrier material. The composite can be prepared by forming a gel or paste of a suitable carrier material, such as aluminum hydroxide, alumina, silica, kieselguhr, magnesium oxide or titanium dioxide to which is added a sulfur containing molybdenum compound in the form of a finely divided powder or a solution or suspension thereof. Suitable sulfur containing molybdenum compounds are for example $MoS_2$, $Mo_2S_5$, $MoS_3$, $MoS_4$, $(NH_4)_2MoS_4$ or mixtures thereof. The activity of the ultimate catalyst may be increased by the presence of such additional members as the platinum group including platinum, palladium, rhodium and ruthenium, as well as cobalt, nickel, rhenium and tungsten. One or more of the additional metal members can be introduced to the carrier prior to, simultaneously with or subsequently to the addition of the sulfur containing molybdenum compound. In general, the additional metal members can be introduced employing impregnation techniques well known to the art as for example by the use of solution of the metal compound illustrated by an aqueous solution of chloroplatinic acid or cobalt nitrate. After thoroughly mixing the carrier and metal compounds, the composite is dried at about 90° to 140° C.

The composite described above is made catalytically active by heat treating at a temperature of about 300° to 700° C., preferably about 450° to 600° C., in an oxidizing atmosphere, suitably air, oxygen or an oxygen enriched gas. The heat treatment providing the active catalyst can be undertaken for periods of from about 1 to 6 hours in the oxidizing atmosphere. Heating of the composite under the activating conditions set forth herein provides the catalyst with the additional metals, when present, in the form of their oxides.

It was extremely surprising to find that the catalysts according to the invention become active only after being tempered by oxygen or an oxygen-containing gas, and it was therefore suspected that the molybdenum sulfides were converted to molybdenum oxides as a result of the tempering. That this is not the case can be seen from Table I which records the results of analysis of the catalyst in regard to its sulfur content. It is believed that an intermediate phase between molybdenum oxide and molybdenum sulfide constitutes the active component of the catalyst.

TABLE I
SULFUR CONTENTS OF THE FRESH, TEMPERED, AND REGENERATED CATALYST

| | |
|---|---|
| 1. Theoretical sulfur content | 5.0 wt. % |
| 2. Measured sulfur content before tempering | 4.7 wt. % |
| 3. Measured sulfur content after tempering | 2.7 wt. % |
| 4. Measured sulfur content after regeneration | 2.2 wt. % |

In general, the novel catalysts described herein are composed of from about 5.0 to 11.0 weight percent molybdenum calculated as the metal, about 3.0 to 7.0 weight percent of sulfur with the remainder being the catalyst support. The additional metal member can be present in amounts of from about 0.2 to 5.0 weight percent of the catalyst calculated as the respective metal oxide. Usually, the platinum group and rhenium component will be present in the range of about 0.2 to 1.0 weight percent. The cobalt, nickel and tungsten members are usually employed at higher levels of from about 2.0 to 5.0 weight percent of the catalyst.

The olefin feed employed by this invention have from 2 to 5 carbon atoms including ethylene, propylene, butenes and pentenes. Mixtures of olefins having the same or different number of carbon atoms can be employed. The olefins are oligomerized into hydrocarbons clear as water of high octane number valuable as gasoline blending components and as chemical intermediates, at temperatures of about 40° C. and higher, pressures of about 5 atmospheres and higher, and at a high speed. In general, the process is conducted at from about 80° to 180° C. at pressures of from about 200 to 1500 p.s.i.g. and at a weight hourly space velocity (w olefin/hr./w catalyst) of about 0.8 to 2.5. The catalysts according to the invention have a long on-stream time and excellent regeneration properties. They can be regenerated by tempering at 300° to 700° C. in a stream of oxygen and/or an oxygen-containing gas. It is technically very easy to handle the catalysts according to the invention, as they are insensitive to oxygen as well as other catalyst poisons. The catalysts may be formed in a desired shape and used in a fixed-bed process but also pulverized and employed in a fluidized-bed or liquid-phase process.

In order to more fully illustrate the nature of this invention and manner of practicing the same, the following examples are presented.

EXAMPLE 1

Finely pulverized $MoS_2$ (30 grams) is admixed with an aluminum hydroxide paste (700 grams) prepared by hydrolytic decomposition of aluminum-secondary-butylate and having a solids content of 25 weight percent. Subsequently, this mixture is homogenized in a kneader for 1 hour. Thereafter, 32.6 grams of cobalt nitrate in 20 milliliters of water are admixed in small portions to the mixture, while the catalyst paste is further homogenized by kneading for 1 hour. The paste is spread onto perforated sheets and dried for 4 hours at 120° C. The catalyst granules thus obtained are tempered for 4 hours at 550° C. in air passing through at the rate of 20 liters per hour. After heating of 27.5 grams of catalyst at a temperature of 600° C. for 6 hours, a 25.7 gram sample was upon analysis found to contain 11.5 weight percent $MoO_3$, 3.5 weight percent CoO and 85.0 weight percent $Al_2O_3$. Basis analysis of the residue and the measured sulfur content of the heat treated catalyst, the catalyst had the following calculated composition: 7.3 weight percent molybdenum as metal, 5.0 weight percent sulfur, 3.5 weight percent cobalt oxide and 84.2 weight percent alumina.

180 milliliters (145 grams) of the above catalyst were loaded into a tubular reactor and 210 grams of propylene per hour were introduced thereto and the reaction conducted at 125° C. and 50 atmospheres. Due to the exothermic reaction the tubular reactor was cooled to maintain the reaction temperature. The propylene feed was quantitatively oligomerized to a colorless, easily mobile liquid ($D_4^{15}$ = 0.775) which was found upon analysis to have the following composition (determined by gas chromatography) after stabilization (Heating the reaction product to 40° C for 30 minutes):

| | |
|---|---|
| $C_4 - C_5$ | 3.4 wt. % |
| $C_6$ | 15.1 wt. % |
| $C_7 - C_8$ | 20.1 wt. % |
| $C_9$ | 33.2 wt. % |
| $C_{10} - C_{11}$ | 13.0 wt. % |
| $C_{12}$ | 6.4 wt. % |
| $> C_{12}$ | 8.8 wt. % |

Spectroscopic tests revealed extensive branching of the obtained oligomers. The $C_6$-fraction, for instance, has the following composition after hydrogenation (at 20° C for 20 minutes using a catalyst comprising 5 wt.% of Pt on A-carbon):

| | |
|---|---|
| 2,3-dimethyl butane | 18.4 wt. % |
| 2,2-dimethyl butane | 4.3 wt. % |
| 2-methyl pentane | 48.0 wt. % |
| 3-methyl pentane | 26.4 wt. % |
| n-hexane | 0.4 wt. % |
| non-identified products | 2.5 wt. % |

When lowering the reaction temperature to about 100° C. and the gas throughput to 150 grams of propylene per hour, primarily $C_6$ and $C_9$ olefins are synthetized, showing an even more extensive branching.

In general, propylene is oligomerized at a temperature of about 40° to 250° C., preferably 120°-180° C. and at a pressure of about 5 to 150 atmospheres, preferably 50-100 atmospheres, and at a weight hourly space velocity of about 0.8 to 2.5. The catalyst has a long lifetime and can easily be regenerated by tempering at 300° to 700° C.

EXAMPLE 2

As in Example 1, 180 milliliters (145 grams) of catalyst were loaded into a tubular reactor and 100 grams per hour of a butene mixture having the following composition:

| | |
|---|---|
| inert materials | 9.4 wt. % |
| butadiene-1,3 | 6.2 wt. % |
| butene-1 | 19.8 wt. % |
| trans-butene-2 | 7.5 wt. % |
| cis-butene-2 | 6.4 wt. % |
| iso-butene | 50.7 wt. % | were introduced thereto and the reaction conducted at 225° C. and 75 atmospheres. Practically all of the butenes were converted to oligomers having the following composition:

| | |
|---|---|
| $C_5$ - $C_7$ | 24.8 wt. % |
| $C_8$ | 36.4 wt. % |
| $C_9$ - $C_{11}$ | 8.8 wt. % |
| $C_{12}$ | 20.1 wt. % |
| > $C_{12}$ | 9.9 wt. % |

Motor and research octane numbers of a fraction including $C_{11}$ free of any additives were respectively 84 and 99.

EXAMPLE 3

A suspension of 49.5 grams of ammonium tetrathiomolybdenate in 66 grams of water and an aqueous Co(NO$_3$)$_2$ solution (32.6 g Co(NO$_3$)$_2$ in 20 ml water) are admixed with an aluminum hydroxide paste (800 grams) prepared by hydrolytic decomposition of aluminum-secondary-butylate and having a solids content of 25 weight percent. This mixture was homogenized in a kneader for 2 hours. Thereafter, the paste was spread onto perforated sheets, dried for 6 hours at 120° C. and subsequently tempered for 4 hours with 20 liters of air per hour at 550° C. The thus prepared catalyst has substantially the same activity as the catalyst prepared according to Example 1.

EXAMPLE 4

(Example of Comparison Using a Supported MoO$_3$ Catalyst)

43.6 grams of ammonium heptamolybdate and 34.0 grams of cobalt nitrate dissolved in a small amount of water are admixed with 800 grams of a 25 percent aluminum hydroxide paste (prepared by hydrolytic decomposition of aluminum-secondary-butylate). This mixture was homogenized in a laboratory kneader for 1 hour. Thereafter, the paste was spread onto perforated sheets, dried for 4 hours at 120° C and subsequently, the dry granules were tempered for 4 hours at 550° C.

The catalyst had the following calculated composition: 85 wt.% of Al$_2$O$_3$; 11.5 wt.% of MoO$_3$; and 3.5 wt.% of CoO 180 ml (141 grams) of this catalyst were loaded into a vertical tubular reactor and propylene was passed therethrough at 150° C and 50 atmospheres, the amount of propylene being 120 liters per hour which corresponds to a catalyst capacity of 0.81 kilogram of propylene per kilogram of catalyst per hour.

Under these conditions, 37.3 percent of the propylene was converted and disproportionated. Only ethylene and butene were obtained. The reaction selectivity amounted to 99 percent. After a test period of 8 hours, only as little as 0.2 gram of polymers per hour was found.

EXAMPLE 5

(Example of Comparison Using a Conventional MoS$_3$ Catalyst)

The catalyst was prepared as described in Example 1 but the addition of MoS$_2$. The catalyst granules were tempered for 4 hours at 550° C in air and thereafter pulverized and admixed with 30 grams of finely pulverized MoS$_2$. By adding a small amount of water to said pulverulent mixture, 3 mm tablets were prepared therefrom in a tableting machine and used in the tests. These tablets were then dried at 120° C for 6 hours.

The catalyst was then tested under the conditions employed in Example 1. The maximum propylene conversion amounted to 0.2 percent (excepting disproportionation) although the catalyst capacity was reduced to 0.5 kilogram of propylene per kilogram of catalyst per hour.

The propylene used in the afore-mentioned Examples 1 to 5 was delivered by a refinery and contained about 0.002 percent by weight of propine and about 50 ppm of sulfur.

EXAMPLE 6

(According to the Invention)

Example 1 was repeated with the exception that a propylene was used that contained substantially no propine and no sulfur. The liquid obtained by this Example had almost the same composition than the one obtained by Example 1. This demonstrates that the catalyst of the invention is insensitive to sulfur and to acetylenic compounds.

We claim:

1. A catalyst comprising sulfur containing molybdenum on a support and suitable for oligomerizing unsaturated hydrocarbons prepared by heating a composite comprising molybdenum sulfide or ammonium tetrathiomolybdenate or mixtures thereof on a support at a temperature of about 300° to 700° C. in an oxidizing atmosphere, said catalyst comprising from about 5.0 to 11.0 weight percent molybdenum, about 3.0 to 7.0 weight percent sulfur and the remainder support.

2. A catalyst according to claim 1 which additionally comprises from about 0.2 to 5.0 weight percent of an oxide of a platinum group metal, cobalt, nickel, rhenium, tungsten or mixtures thereof.

3. A catalyst according to claim 2 wherein said additional metal oxide is cobalt oxide, nickel oxide or tungsten oxide and comprises from 2.0 to 5.0 weight percent of said catalyst.

4. A catalyst according to claim 1 wherein said composite support is aluminum hydroxide, alumina, silica, kieselguhr, magnesium oxide or titanium dioxide.

5. A catalyst according to claim 1 wherein from about 2.0 to 5.0 weight percent cobalt oxide is associated with said catalyst and where said support is alumina.

* * * * *